United States Patent
Wickstead et al.

(10) Patent No.: US 7,225,689 B2
(45) Date of Patent: *Jun. 5, 2007

(54) SAMPLE TESTING DEVICE WITH FUNNEL COLLECTOR

(75) Inventors: James C. Wickstead, Mendham, NJ (US); Keith A. Seritella, Washington, NJ (US); Lawrence Salvo, Miami Beach, FL (US); Stephen Berkman, Miami Beach, FL (US); Luis Agudelo, Miami Beach, FL (US)

(73) Assignee: Rapid Medical Diagnostic Corporation, North Bay Village, FL (US)

( * ) Notice: Subject to any disclaimer, the term of this patent is extended or adjusted under 35 U.S.C. 154(b) by 66 days.

This patent is subject to a terminal disclaimer.

(21) Appl. No.: 10/948,861

(22) Filed: Sep. 24, 2004

(65) Prior Publication Data
US 2005/0142031 A1    Jun. 30, 2005

Related U.S. Application Data

(60) Provisional application No. 60/512,875, filed on Oct. 20, 2003.

(51) Int. Cl.
*G01N 1/18* (2006.01)
(52) U.S. Cl. ............... 73/863.23; 422/61; 422/58; 422/101; 436/169; 436/178

(58) Field of Classification Search ............. 73/863.23, 73/863.21, 863.51; 422/58, 61, 101; 436/169, 436/178
See application file for complete search history.

(56) References Cited

U.S. PATENT DOCUMENTS

| | | | | |
|---|---|---|---|---|
| 5,935,864 A * | 8/1999 | Schramm et al. | ............. | 422/61 |
| 6,248,294 B1 * | 6/2001 | Nason | ............. | 422/61 |
| 6,634,243 B1 * | 10/2003 | Wickstead et al. | ............. | 422/61 |
| 6,660,527 B2 * | 12/2003 | Stroup | ............. | 422/61 |
| 6,991,898 B2 * | 1/2006 | O'Connor | ............. | 435/4 |
| 2003/0064526 A1 * | 4/2003 | Niedbala et al. | ............. | 422/61 |
| 2003/0180815 A1 * | 9/2003 | Rawson et al. | ............. | 435/7.9 |
| 2005/0136553 A1 * | 6/2005 | Kaylor et al. | ............. | 436/518 |
| 2005/0180882 A1 * | 8/2005 | Tung et al. | ............. | 422/61 |

FOREIGN PATENT DOCUMENTS

WO    WO 2005045408 A1 *    5/2005

* cited by examiner

*Primary Examiner*—Hezron Williams
*Assistant Examiner*—Nashmiya Fayyaz
(74) *Attorney, Agent, or Firm*—Townsend and Townsend and Crew LLP

(57) ABSTRACT

The present invention provides a funnel collector for use with a sample testing device. The funnel collector collects and holds a fluid sample in order to place the sample in immediate contact with a diagnostic test strip, which reacts with the sample in a known fashion.

23 Claims, 8 Drawing Sheets

SAMPLE TESTING DEVICE WITH FUNNEL COLLECTOR

The present application claims the benefit of U.S. Provisional Application No. 60/512,875, filed Oct. 20, 2003, entitled SAMPLE TESTING DEVICE WITH FUNNEL COLLECTOR, which is incorporated herein by reference.

BACKGROUND OF THE INVENTION

1. Field of the Invention

The present invention relates generally to an apparatus for collecting, processing and analyzing a liquid specimen in a fully integrated system. In particular, the present invention relates to a funnel collector for use with a sample testing device.

2. Description of Related Art

Diagnostic testing throughout the world is currently carried out using a variety of different specimen types. Many of the samples tested, such as whole blood, serum, oral fluid, plasma, cerebrospinal fluid and others, are liquid.

Testing for infectious diseases under laboratory conditions typically involves use of a blood serum specimen obtained by removing the blood cells from an intravenous blood sample by centrifugation. The sample is first drawn from the patient by a trained phlebotomist. The serum sample so obtained is then tested under laboratory conditions using one of a number of methodologies, such as Enzyme Linked Immuno Sorbent Assay (ELISA), Immunofluorescence (IFA), Latex Agglutination (LA), or any of a number of automated instrument platforms employing chemiluminescence, fluorescence or other sensitive technologies. As there are other known diagnostic technologies in place, this is by no mean an exhaustive list.

Although serum testing under laboratory conditions has traditionally constituted the technique of choice, there is now a growing trend to move testing closer to the patient and use alternative specimen matrices such as whole blood and others. In other words, the sample is drawn from the patient, processed and analyzed more rapidly, often while the patient is still in attendance. The recent advance known as "near-patient" or "point-of-care" testing has caused a major shift in the way testing is done. Statistics show growth of over 20% per annum in this mode of testing for each of the last four years.

Such growth in this mode of testing has resulted in the increased use of alternate specimen types (e.g. whole-blood or oral fluid) not requiring the use of trained phlebotomists or additional steps to separate red blood cells from the required specimen. Rather, the sample can be drawn from the patient and processed directly. As a consequence, results can now be obtained, analyzed and conveyed to the patient while the patient or subject is still in the presence of the healthcare provider. This avoids the need for repeat patients or the need for the patient to contact the healthcare provider at a future time to obtain their test results.

Point-of-care (POC) testing therefore offers the advantage of giving the physician (and, if the physician chooses, the patient) immediate results, in contrast to conventional testing, where there is a waiting period, that could be anywhere from several hours to weeks, during which the specimens are transported to a laboratory testing facility, processed, and results sent to the physician.

It is standard in the industry to confirm infectious disease test results by repeat testing, often by a more sensitive methodology, especially when the testing is for potentially life-threatening diseases such as HIV, Hepatitis C, Hepatitis B, and so on. This applies regardless of whether the testing is performed in a laboratory or at the point-of-care. The second test used to confirm the result of the primary test is known as a "confirmatory" or "confirmation" test and typically uses a different methodology to confirm a diagnosis or otherwise. For instance in HIV diagnostics, Western Blot or ELISA methods may be used. In all instances a second specimen will be required. Owing to the serious nature of such testing, anything that can expedite sample processing is of tremendous importance.

In the case of laboratory testing, there may be sufficient specimen material remaining from the initial blood draw to carry out confirmation testing.

However, no rapid (in-office) tests are known which include a mechanism to collect a specimen for confirmatory testing at the time of the first patient visit to the healthcare facility.

SUMMARY OF THE INVENTION

The present invention is directed to a funnel collector for use with a sample testing device which serves to collect and hold a liquid specimen in order to place the specimen in immediate contact with a diagnostic test strip, which then reacts with the specimen in known fashion. The sample testing device also has a buffer container that can contain buffer fluid therein, the test strip, an end of which is held by the funnel collector, a test strip container having a receptacle dimensioned and disposed to accommodate a filter so that when the filter is held therein the test strip is disposed in the receptacle, and a sample collector for holding a sample.

In one embodiment, the sample collector is shaped to receive the buffer container, and the sample collector has a channeling member and a piercing member which, when the buffer container is placed in the sample collector, pierces the buffer container so that the buffer fluid in the buffer chamber contacts the sample and passes through the lumen to the funnel collector. As buffer fluid flows through the lumen of the sample collector the buffer fluid that has contacted the sample collects in the funnel collector and contacts the test strip.

BRIEF DESCRIPTION OF THE DRAWINGS

The particular features and advantages of the invention as well as other objects will become apparent from the following description taken in connection with the accompanying drawings, in which.

DETAILED DESCRIPTION OF THE PREFERRED EMBODIMENT

As depicted in the accompanying drawings, the present invention is directed to a compact, self-contained testing device which can be used to obtain and analyze fluid samples, and more particularly, samples of bodily fluid. More specifically, the present invention is directed to a funnel collector for use with a sample testing device, such as the sample testing device shown and described in U.S. Pat. No. 6,634,243 to Wickstead, et al. The funnel collector serves to collect and hold fluid samples in order to place the sample in immediate contact with a diagnostic test strip. The sample testing device can include an elongated body portion which accommodates a test strip, a buffer container which holds material that first reacts with the sample and then reacts with the test strip to indicate the results of the test, and a sample collector which serves to combine the material in the buffer container with the sample.

Construction of the Funnel Collector

Figure 1:
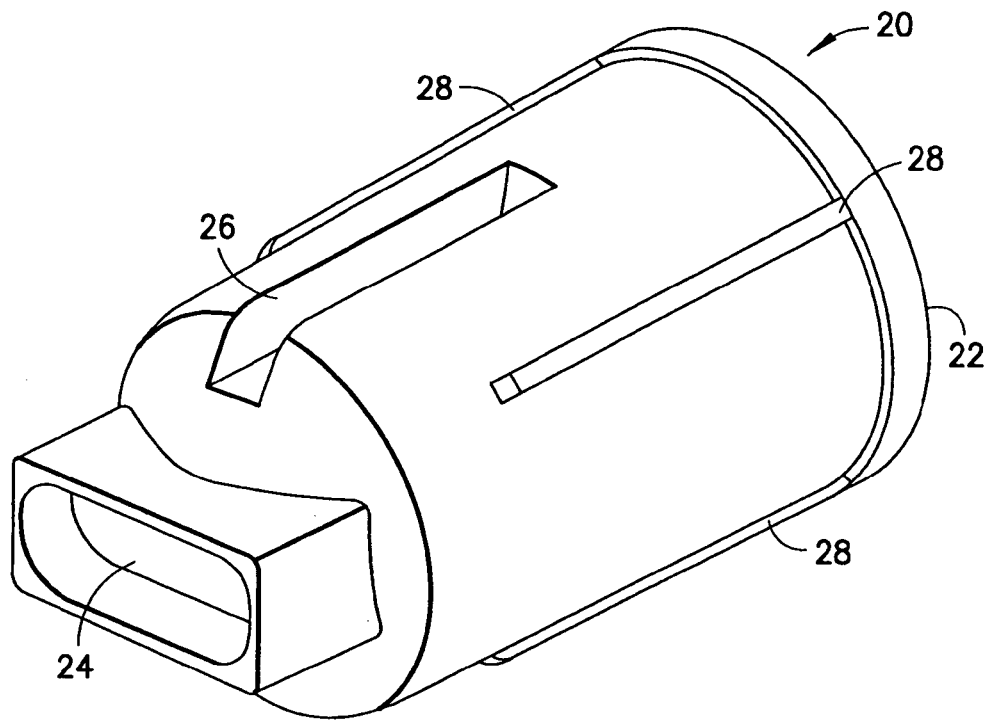
FIG. 1 is a perspective view of a funnel collector for use with a sample testing device according to one embodiment of the present invention.

FIG. 1 depicts a funnel collector according to one embodiment of the present invention.

Funnel collector 20 has both a top opening 22 and a bottom opening 24. Top opening 22 is circularly shaped to receive a sample collector. Bottom opening 24 is rectangularly shaped to receive a test strip, one end of which is secured in funnel collector 20.

In one embodiment of the present invention, funnel collector 20 can have grooves 26 and protrusions 28 on the outer surface for engaging corresponding protrusions and grooves, respectively, on a test strip container (shown in FIG. 5), so that the test strip container and funnel collector 20 are connected in a fluid-tight manner.

In an alternate embodiment of the present invention, funnel collector 20 can have a threaded outer surface, which is arranged to engage matching threads formed on the inner surface of a test strip container. Other schemes for obtaining a fluid-tight connection between funnel collector 20 and a test strip container can be used. For example, a fluid-tight press fit between two smooth surfaces, i.e., outer surface of funnel collector and the inner surface of a test strip container can be used. That is, the outer diameter of funnel collector 20 and the inner diameter of a test strip container are sized so that, when joined, funnel collector 20 and the test strip container frictionally engage one another.

The dimensions and size of funnel collector 20 can vary. However, funnel collector 20 should be sized to maintain a fluid-tight connectivity with the other components of the sample testing device and to securely hold a test strip.

Funnel collector 20 can be made of any material, but preferably is made from a non-porous, inert, biocompatible material such as, for example, a polymer or stainless steel. Funnel collector 20 can also be constructed of one material and coated with a non-porous, biocompatible material such as, for example, a polymer resin such as the one manufactured by Dupont and marketed under the name TEFLON.

Figure 2:
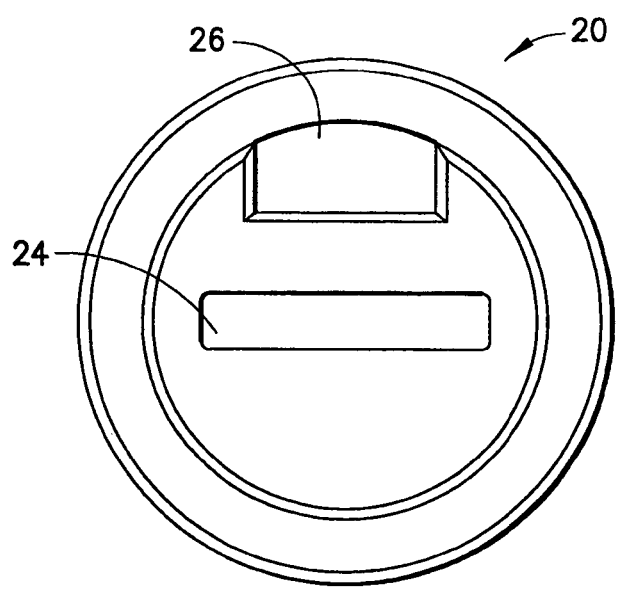
FIG. 2 is a front plan view of a funnel collector for use with a sample testing device according to one embodiment of the present invention.
Figure 3:
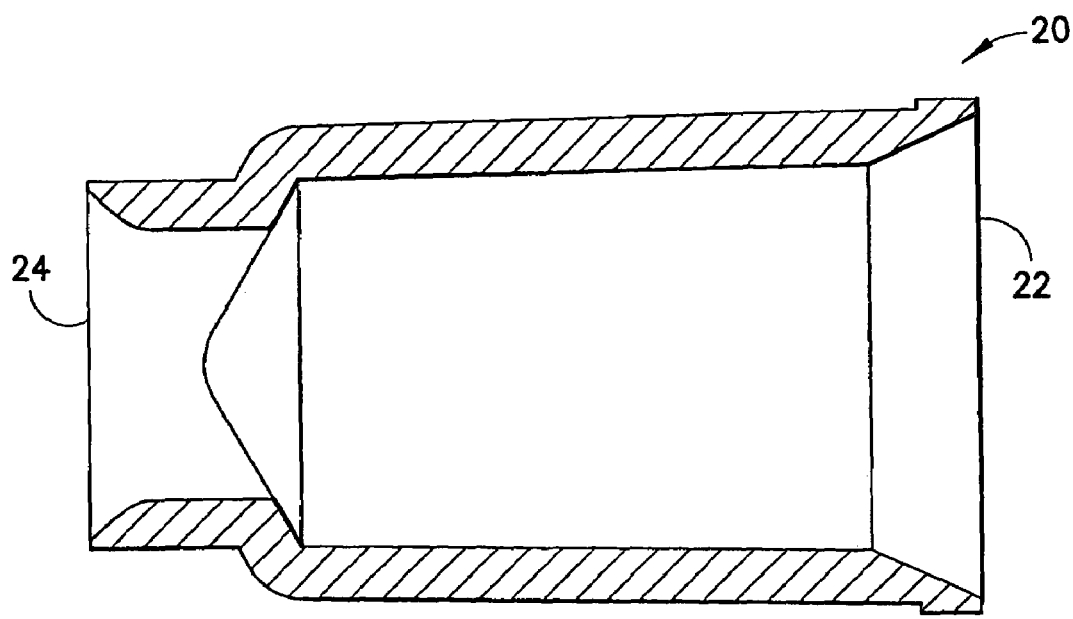
FIG. 3 is a top plan view of a funnel collector for use with a sample testing device according to one embodiment of the present invention.
Figure 4:
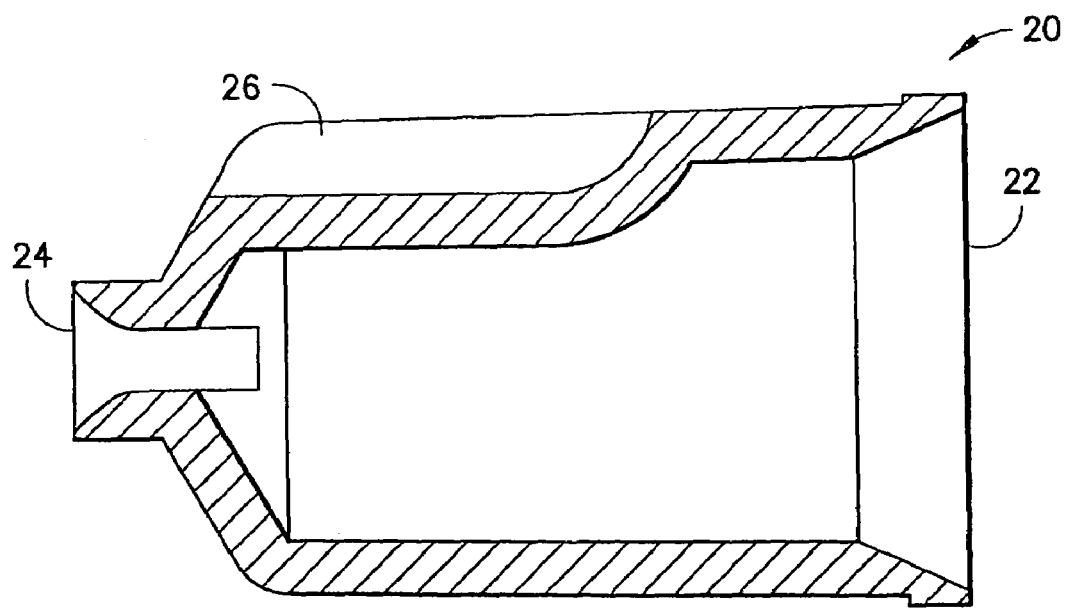
FIG. 4 is a side plan view of a funnel collector for use with a sample testing device according to one embodiment of the present invention.

FIGS. 2, 3, and 4 depict funnel collector 20 of the present embodiment.

Construction of the Sample Testing Device with Funnel Collector

Figure 5:
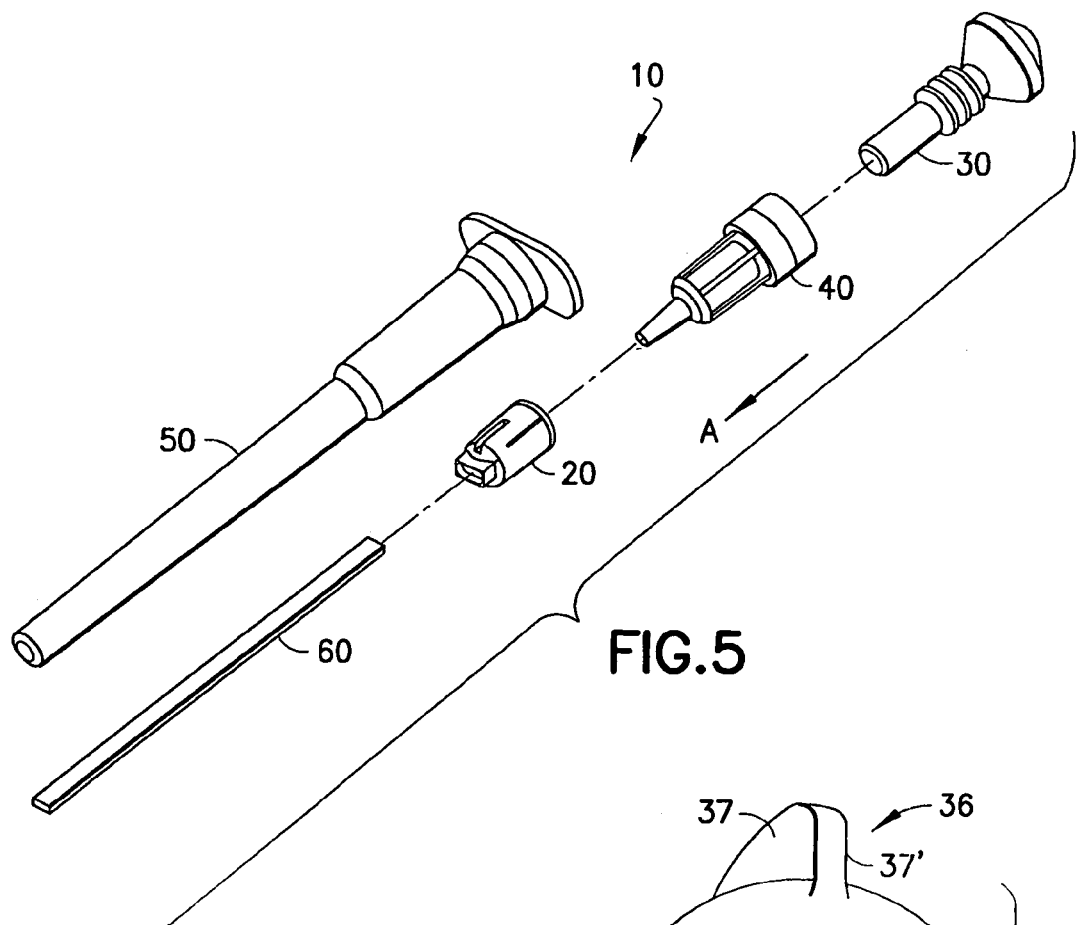
FIG. 5 is an exploded perspective view of a sample testing device with funnel collector according to one embodiment of the present invention.
Figure 6:
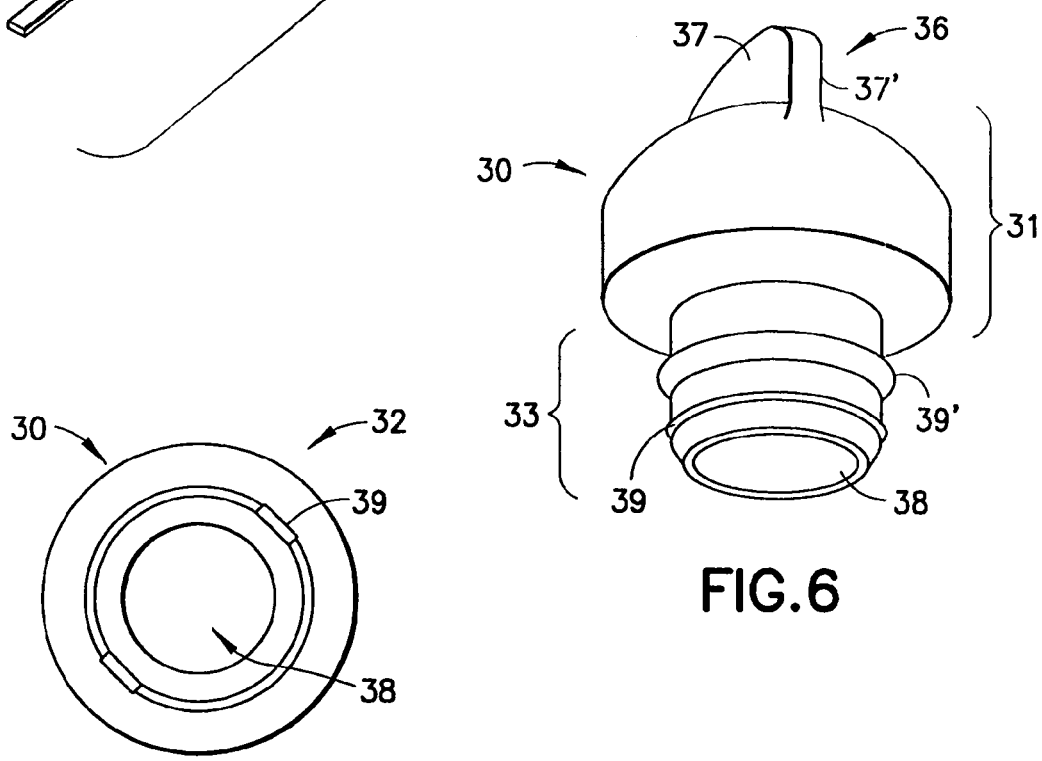
FIG. 6 is a perspective view of the front and a portion of the perimeter of a buffer container for use with a sample testing device according to one embodiment of the present invention.
Figure 7:
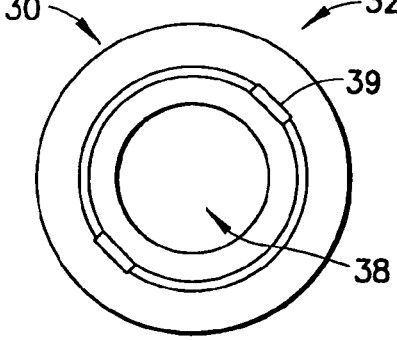
FIG. 7 is a bottom plan view of the buffer container depicted in FIG. 6.
Figure 8A:
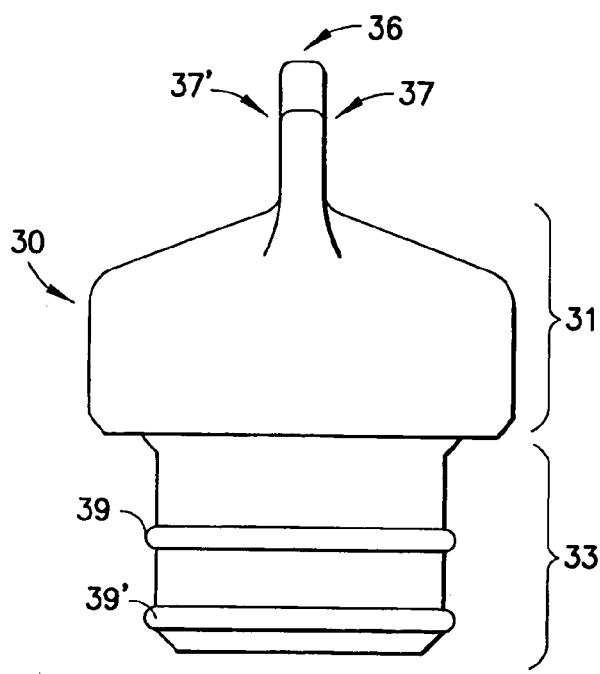
FIG. 8A is a side elevational view of the buffer container depicted in FIG. 6.
Figure 8B:
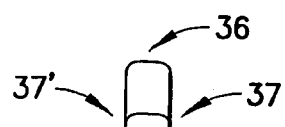
FIG. 8B is a side elevational view of an alternate buffer container.
Figure 9:
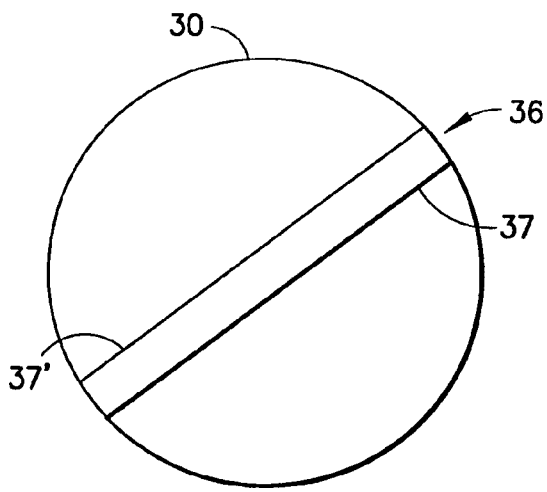
FIG. 9 is a top plain view of the buffer container depicted in FIG. 6.

FIG. 5 depicts, in exploded form, a sample-testing device, 10, with funnel collector 20 according to one embodiment of the present invention. Sample testing device 10 includes funnel collector 20 as well as, a buffer container 30, a sample collector 40, a test strip container 50, and a test strip 60. Each of these components will be discussed in turn.

As shown in FIGS. 6 through 9, buffer container 30 is a plug-shaped, generally cylindrical, member having a top portion 31, a base portion 32, a body portion 33, and a pierceable membrane 38. The buffer container 30 is hollow and, when loaded into the sample device for testing, contains a buffer fluid (not shown).

By way of non-limiting example, the top portion 31 of buffer container 30 is preferably contoured, with a compressible grip 36 having side walls 37 and 37'. The benefits of this arrangement will be discussed hereafter.

In one embodiment of the present invention, buffer container 30 and sample collector 40 are initially held in place by a press and snap detent 39. A second press and snap detent 39' holds and seals buffer container 30 in firm contact with sample collector 40 when buffer container 30 is pressed downward onto piercing edge 44 of piercing member 43, thereby puncturing pierceable membrane 38 and releasing the buffer fluid housed in buffer container 30. See FIG. 8A.

In an alternate embodiment of the present invention, body portion 33 of buffer container 30 has a threaded outer surface 34 which is arranged to engage matching threads formed on the inner surface 41 of sample collector 40. This way, buffer container 30 can be joined to sample container 40 in fluid-tight fashion. See FIG. 8B. Other schemes for obtaining a fluid-tight connection, such as forming elastic projections (not shown) on or applying one or more O-rings to the body portion 33 also could be employed. Alternatively, a fluid-tight press fit between smooth surfaces also could be used.

Preferably, the outer diameter of sample collector 40 and the inner diameter of buffer container 30 are sized so that, when joined, sample collector 40 and buffer container 30 frictionally engage one another.

Other shapes and arrangements of elements for joining buffer container 30 and sample collector 40 are also suitable, provided such elements allow for fluid communication between buffer container 30 and sample collector 40.

Pierceable membrane 38 of buffer container 30 forms a frangible, fluid impermeable barrier for retaining buffer fluid in the buffer container 30. Pierceable membrane 38 may be formed of any non-reactive material which is capable of containing the buffer fluid in buffer container 30 and which can be pierced by piercing edge 44 of the piercing member 43 formed in the sample collector 40. Examples of materials suitable for forming pierceable membrane 38 include, but are not limited to, metal foil, polymeric membrane, glass, or plastic. Also, the pierceable membrane 38 could be formed with a suitably sized and shaped score or pre-stressed area (not shown) which will rupture when contacted by piercing edge 44.

Figure 10:
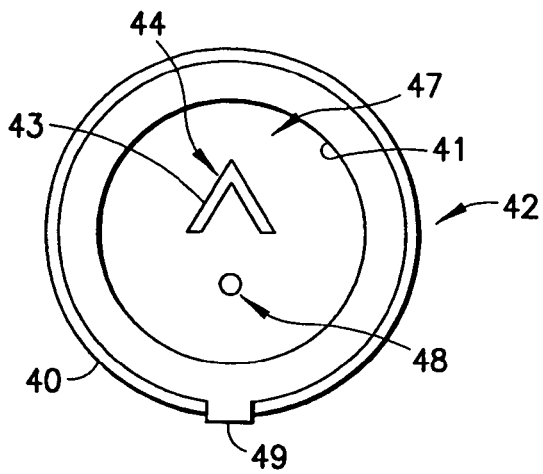
FIG. 10 is a top plain view of a sample collector for use with a sample testing device according to one embodiment of the present invention.
Figure 11:
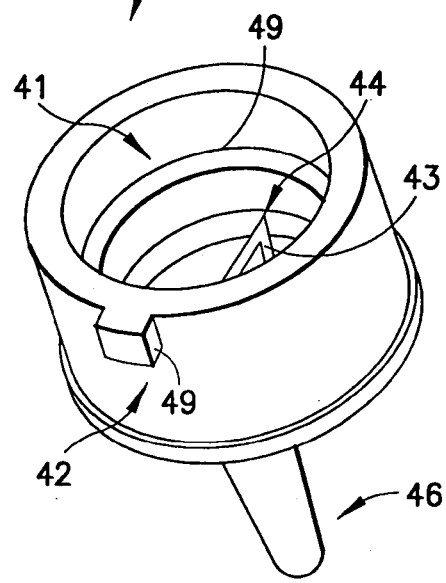
FIG. 11 is a perspective view showing the top and a portion of the perimeter of the sample collector depicted in FIG. 10.

With reference now to FIGS. 10 and 11, sample collector 40 includes an inner surface 41, an outer surface 42, and an interior base 47. Sample collector 40 also includes piercing member 43. The upper edge of piercing member 43 includes a sharp piercing edge 44 that contacts and pierces pierceable membrane 38 of buffer container 30 when buffer container 30 is joined to sample collector 40, thereby releasing the buffer fluid (not shown). Piercing member 43 could be shaped to facilitate the flow of buffer fluid.

With continued reference to FIGS. 10 and 11, sample collector 40 also includes an elongated and hollow channeling member 46. The lumen 48 runs from the tip of the channeling member 46 to the base 47 of sample collector 40, for reasons explained hereafter.

Test strip container 50 will now be described with reference to FIGS. 5 and 12.

Test strip container 50 serves several different functions. First, it holds all of the other components of sample testing device 10. Second, during use, test strip container 50 holds the sample and buffer fluid as they mix and are drawn into contact with test strip 60. Third, test strip container 50 isolates the sample and buffer fluid from the environment.

Figure 12:
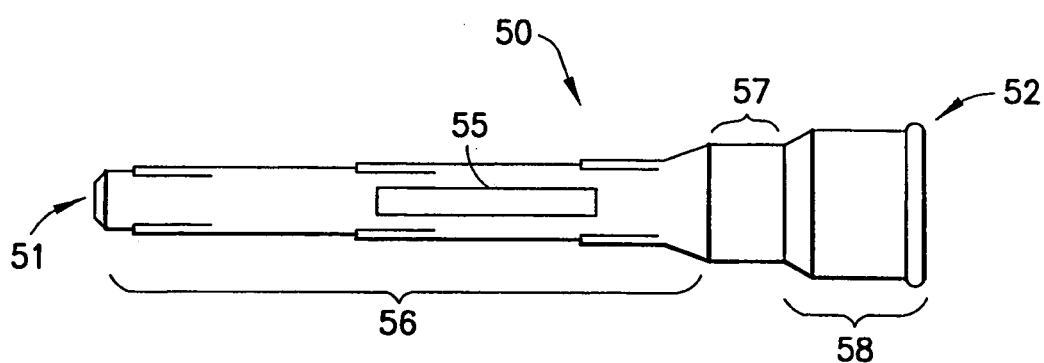
FIG. 12 is a side elevational view of a test strip container for use with a sample testing device according to one embodiment of the present invention.

With continued reference to FIGS. 5 and 12, test strip container 50 is preferably a generally cylindrical container closed at its bottom end 51 and open at its open end 52 to enable loading with all of the components of sample testing device 10. Since test strip container 50 holds funnel collector 20, buffer container 30, sample collector 40, and test strip 60, the profile of test strip container 50, seen from the side as in FIG. 12, can be stepped. This way, each stepped region is approximately the same size as the part of sample testing device 10 which it contains. The longest and narrowest part of test strip container 50 is chamber 56, which corresponds to test strip 60. Portion 57 of test strip container 50 corresponds to and holds funnel collector 20 and is somewhat wider than chamber 56. Portion 58 of test strip container 50 is in turn somewhat wider than portion 57, and corresponds to and holds buffer container 30.

As shown in FIG. 12, test strip container 50 is closed at bottom end 51 and open at end 52. Test strip container 50 is sized at position 57 to accommodate funnel collector 20 and test strip 60 which is secured within funnel collector 20. Test strip container 50 is dimensioned at position 58 to securely hold sample collector 40 and buffer container 30 by a friction fit. By way of non-limiting example, buffer container 30 and sample collector 40 could be welded or bonded into place. Also, buffer container 30 can be joined to sample collector 40 before sample collector 40 and buffer container 30 are inserted into test strip container 50.

As shown in FIG. 5, test strip 60 can itself be a test strip such as are known. Such test strips are customarily treated with a reagent compatible with the test being performed.

If, as is preferred, test strip 60 is a visual test strip, meaning the results of the test are determined by observing a visual indication on the test strip, test strip container 50 should be constructed so that test strip 60 can be viewed. This can be done by forming the entire test strip container 50 from transparent material such as glass or plastic. Alternatively, opaque or non-transparent material could be used and at least one transparent window 55 could be formed in the chamber 56 of the test strip container 50 so that test strip 60 can be viewed therethrough.

Test strip container 50 can be made from any suitable nonreactive material, such as glass, plastic or ceramic, or a combination thereof. Test strip container 50 can be formed using any known technique. Injection molding of glass or plastic is presently thought to be preferable.

Sample testing device 10 is preferably packaged in a sterile fashion with all, or at least some, of its components, funnel collector 20, buffer container 30, sample collector 40, test strip container 50, and test strip 60 assembled together. It will be appreciated that because sample collector 40 includes a piercing member 43 designed to pierce membrane 38 of buffer container 30 and allow the buffer fluid therein to run out, a protective piece such as a flat disc of material that must be removed before use can be provided between sample collector 40 and buffer container 30. This way, membrane 38 will not be ruptured inadvertently. Alternatively, those components can be packaged in unassembled form for later assembly by the user. Sterilization and packaging can be accomplished using any suitable technique now known or hereafter developed.

Although it is presently thought to be preferable to provide buffer container 30 of sample testing device 10 loaded with the buffer fluid, buffer container 30 can be provided empty for filling with buffer fluid by the user. In such an arrangement, buffer container 30 could be made entirely or just in part from a self-sealing material. To fill buffer container 30, the user could take a hypodermic syringe containing a sufficient amount of the buffer fluid, and drive the syringe needle through the self-sealing material. Once the needle is inside buffer container 30, the user would inject the buffer fluid into the buffer container and withdraw the needle therefrom. The self-sealing material then closes the opening made by the needle, retaining the buffer fluid inside the buffer container.

An alternate embodiment of the present invention will now be described with reference to FIGS. 13 and 14.

Figure 13:
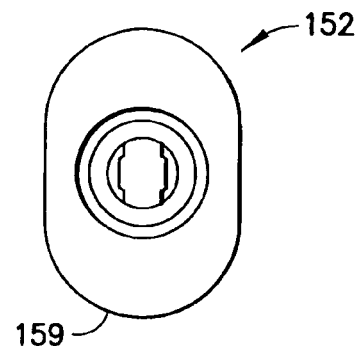
FIG. 13 is a top plan view of the test strip container depicted in FIG. 12.
Figure 14:
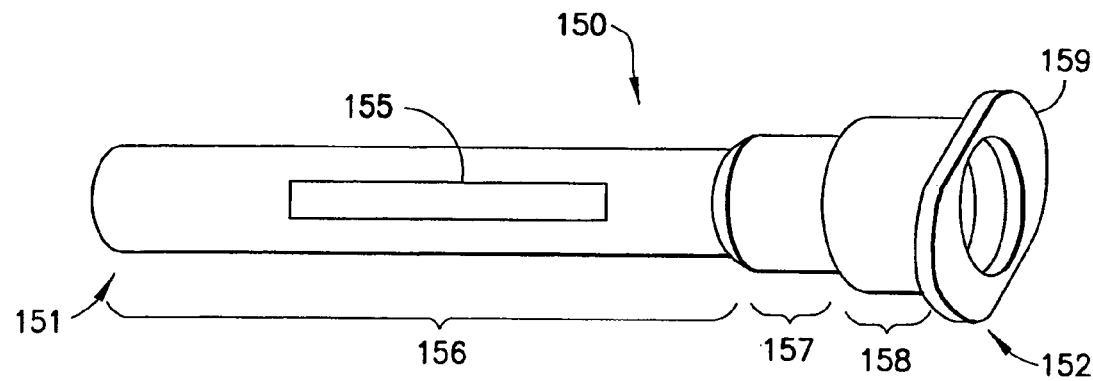
FIG. 14 is a side elevational view of the test strip container depicted in FIG. 12.

As depicted in FIGS. 13 and 14, the open end 152 of test strip container 150 has been modified to include a flange 159 extending outward in a plane generally perpendicular to the long axis of test strip container 150. By way of non-limiting example, flange 159 can be oval, as depicted, or round (not shown). Flange 159 helps the person using a sample testing device grasp test strip container 150. Flange 159 also prevents test strip container 150 from rolling and provides a flat surface on the back of test strip container 150 for marking or writing.

Figure 15A:
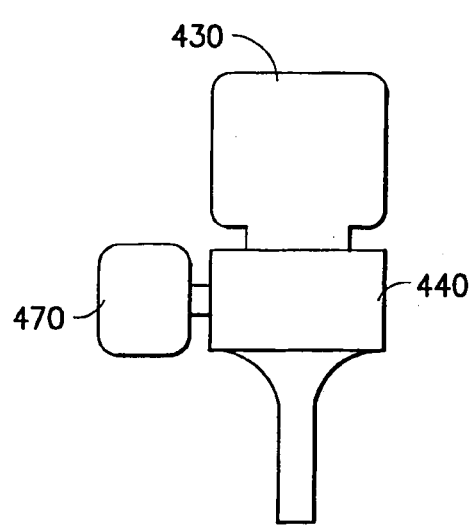
FIG. 15A is a front elevational view of an alternate buffer container and sample collector that can be used in accordance with the present invention.
Figure 15B:
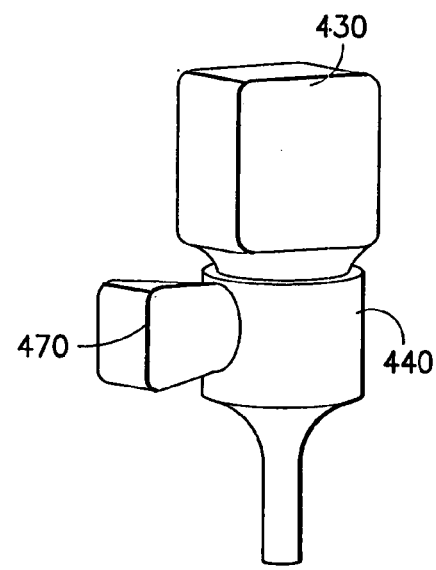
FIG. 15B is a perspective view showing the front, one side and top of an alternate buffer container and sample collector that can be used in accordance with the present invention.

Another embodiment of the present invention is depicted in FIGS. 15A and 15B. FIGS. 15A and 15B illustrate the interaction among buffer container 430, sample collector 440 and pump 470. Pump 470 is preferably made of an elastic or polymeric material which is capable of being compressed by squeezing so as to expel air therefrom. Releasing the pump 470 then draws air or other fluid toward the pump.

Figure 16:
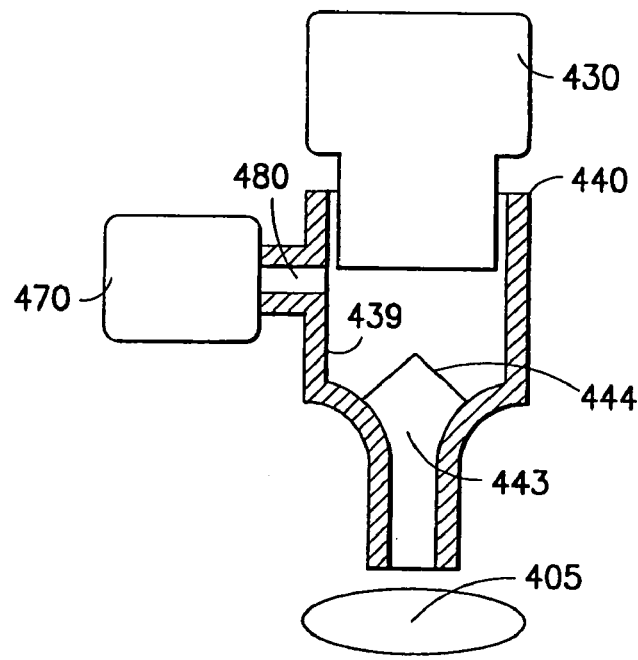
FIG. 16 is a front elevational view in cross-section of the buffer container and sample collector depicted in FIG. 15A and 15B.

As shown in FIG. 16, a portion of sample 405 is drawn into sample collector 440 when compressed pump 470 is released thereby creating a vacuum in sample collector 440. Sample 405 flows into sample collector 440 to fill the vacuum created by the release of pump 470. After sample 405 is drawn into sample collector 440, sample collector 440 is placed inside a test strip container atop a funnel collector. The funnel Collector has a fluid-tight fit with the test strip container thereby ensuring that any liquid which contacts a test strip has collected in the funnel collector.

Buffer container 430 is then inserted into sample collector 440. Buffer container 430 fits securely into sample collector 440 and seals air passage 480 thereby inhibiting the operation of pump 470. Sample collector 440 has at least one piercing edge 444 on a piercing member 443. Piercing edge 444 pierces buffer container 430 thereby releasing the buffer fluid contained within. The buffer fluid mixes with sample 405 and the resulting mixture collects in a funnel collector.

Buffer container 430 can be held in place in sample collector 440 by a press and snap detent 439. A comparable second press and snap detent (not shown) secures buffer container 430 in firm contact with sample collector 440 once buffer container 430 is pressed downward onto piercing edge 444 of piercing member 443, thereby puncturing the pierceable membrane (not shown) and releasing the buffer fluid housed in buffer container 430. See FIG. 16. The detent can provide a fluid-tight seal between buffer container 430 and sample collector 440. Again, any other known or discovered sealing can be used.

Figure 17:
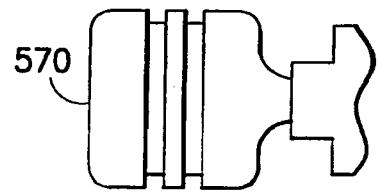
FIG. 17 is a side elevational view of an alternate pumping mechanism.

FIG. 17 depicts an alternate embodiment of pump 470 wherein pump is accordion-shaped 570.

Figure 18:
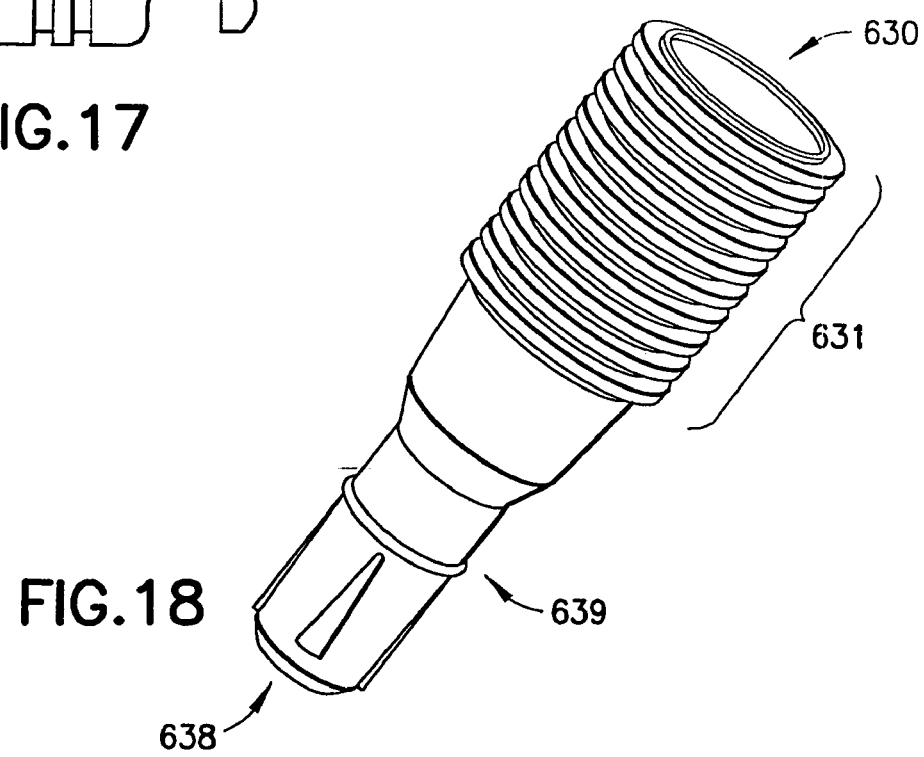
FIG. 18 is a perspective view showing the front and top of a cylindrical buffer container that may be used with the present invention.

FIG. 18 depicts an alternate buffer container 30 wherein the buffer container 630 has a bellowed top portion 631 in order to facilitate expulsion of the buffer solution from buffer container 630 into the sample collector (not shown). Buffer container 630 is initially secured to the sample collector by the interaction of raised ring 639 with a matching groove (not shown) formed in the sample collector (not shown). The sample collector can include a second depression (not shown) which holds and seals buffer container 630 in firm contact with the sample collector when buffer container 630 is pressed downward onto the piercing edge of the piercing member, thereby puncturing pierceable membrane 638 of buffer container 630 and releasing the buffer fluid housed in buffer container 630.

By pressing downward and compressing the bellows region 631 of buffer container 630, pierceable membrane 638 of buffer container 630 is pierced by the piercing edge (not shown) of the piercing member (not shown). Liquid in the buffer container 630 then flows out of buffer container 630 and into sample collector (not shown) under the influence of gravity. In a further embodiment, pierceable membrane 638 of buffer collector 630 can have a weakened portion (not shown) where it will fail when stressed by the raised pressure of the liquid inside the compressed bellows 631.

Figures 19, 20:
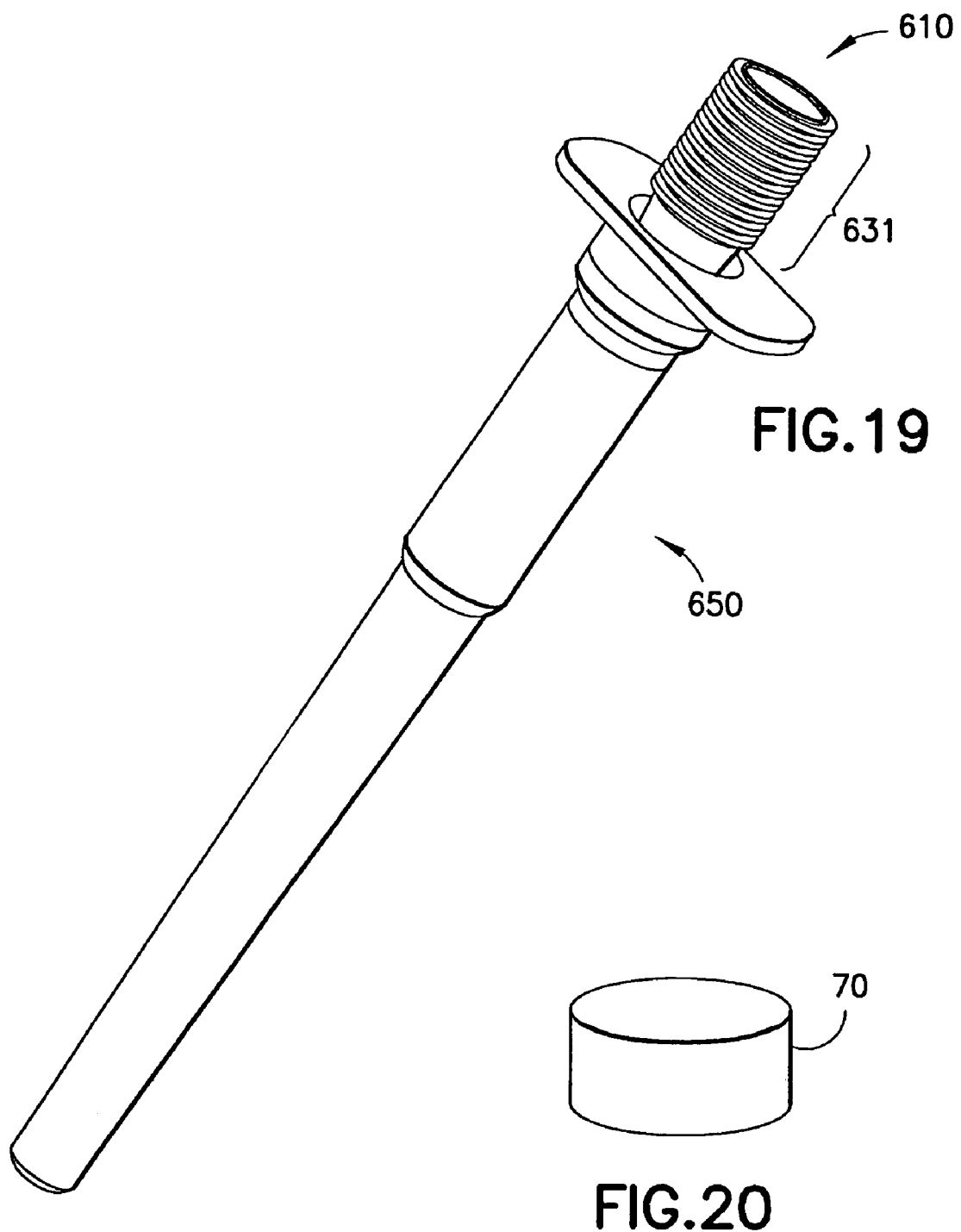
FIG. 19 is a perspective view depicting the alternate buffer container of FIG. 18 used with the sample testing device of the present invention.
FIG. 20 is a perspective view showing an anti-splashback disc that may be used with the present invention.

FIG. 19 illustrates buffer container 630 loaded into a sample testing device 610 comparable to that depicted in FIGS. 13 and 14. Buffer container 630 is tapered so that bellows 631 of buffer container 630 does not fit in the open end of test strip container 650.

It should be understood that while various components described above have been shown as being circular in cross-section, this geometry is merely preferable, and not required. Other shaped components could also be used without departing from the present invention.

In an alternate embodiment of the present invention, with reference to FIG. 5, sample testing device 10 further comprises an anti-splashback disc 70 (shown in FIG. 20) which sits within top opening 22 of funnel collector 20 and below sample collector 40. Anti-splashback disc 70 controls the flow of the sample, e.g., blood, as it approaches and collects in funnel collector 20. More specifically, initially, anti-splashback disc 70 diffracts the initial surge of sample from sample collector 30 in order to lessen the impact of the sample off the sides of funnel collector 20 consequently reducing the deflection of sample off of funnel collector 20. Second, anti-splashback disc 70 traps any sample that may have deflected off of funnel collector 20 thereby maximizing the amount of sample that is ultimately delivered to test strip 60.

Anti-splashback disc 70 can be made of any material, but preferably is made from a porous, non-reactive, biocompatible material. The material of anti-splashback disc 70 should have a sufficient porosity to conduct the sample to funnel collector 20; however, have an adequate density to trap as much deflected sample as possible and sufficient hydrophobic properties to release as much sample into funnel collector 20 as possible.

Use of the Sample Testing Device

The present invention functions by mixing a test sample with a buffer fluid, collecting the mixture, and then absorbing the mixture using a piece of reactive test material, i.e. a test strip. A reactive test material is a material which changes one or more properties when in the presence of a specific substance. Here, the properties which change are preferably visual. By way of non-limiting example, the test strip can change color or develop one or more lines, bands, dots or patterns when certain materials are applied thereto. The precise manner in which this is accomplished will be discussed.

Once sample testing device 10 has been removed from its packaging it can be prepared for use as follows.

A sample of material (not shown) to be tested is introduced into sample collector 40. Examples of fluids which may be used as samples in the testing system of the present invention include, but are not limited to, saliva, cerebrospinal fluid, serum, whole blood, plasma, vaginal fluid, semen, and urine. These bodily fluids may be obtained from either humans or animals. In addition, fluids obtained from plants, trees, soil, the environment and other sources may be used as samples. Depending upon the nature of the sample, the sample can be loaded into the sample collector 40 in any of several ways.

If the liquid is not overly viscous, it can be drawn upward into lumen 48 of channeling member 46 through capillary action. By way of example, the tip of channeling member 46 can be dipped into a patient's blood, where it will be drawn up into lumen 48. In some cases, the patient may be bleeding freely, for example, if the patient has a cut or open wound. Alternatively, it may be necessary or preferred to draw blood from the patient. This can be done by jabbing the patient, say, in a finger, toe or earlobe, with a sharp needle. After a large drop of blood has collected, the tip of channeling member 46 is dipped into the blood drop, and capillary action will draw that blood up into lumen 48 of channeling member 46.

Since capillary action is determined by the viscosity of the liquid in question and the dimensions and composition of the material forming the capillary, the shape of lumen 48 and the composition of channeling member 46 can be selected so that the liquid to be tested will be drawn through capillary action into lumen 48. The viscosity of the liquid to be tested will therefore determine the construction of channeling member 46.

If the material to be tested is a liquid and it is held in a container, such as a beaker or test tube, the tip of channeling member 46 can be dipped into the liquid. Liquid will then be drawn into lumen 48 by capillary action.

Alternatively, drops of the liquid sample can be placed into lumen 48 by dripping the liquid onto base 47 of sample collector 40. Again, capillary action will draw the liquid into lumen 48. This approach may be preferred where the liquid to be tested is contained in a syringe or pipette.

If the material to be tested is highly viscous or even solid, the material can be dropped onto base 47 of sample collector 40.

Once the sample is held by sample collector 40, the sample is exposed to the buffer fluid held in buffer container 30, whether with or without agitation such as shaking. This requires the buffer fluid held within buffer container 30 be allowed to flow out and come into contact with the sample.

With reference now to FIG. 5, this can be done by positioning buffer container 30 in sample collector 40 so that membrane 38 of buffer container 30 is pierced by piercing edge 44 of piercing member 43. If buffer container 30 and sample collector 40 have matching threads 39 and 49, respectively, this can be effected by positioning buffer container 30 and sample collector 40 together so that threads 39 and 49 are positioned for mating engagement. By then grasping compressible grip 36 of buffer container 30 and twisting, threads 39 and 49 will engage and, owing to relative rotation therebetween, draw buffer container 30 toward the base 47 of sample collector 40. As buffer container 30 moves toward the sample collector, pierceable membrane 38 is pierced by piercing edge 44 of piercing member 43. Liquid in buffer container 30 can then flow outward and downward under the influence of gravity and come into contact with the sample held in sample container 40.

If desired, pierceable membrane 38 of buffer container 30 can have a weakened portion (not shown) where it will, when stressed, fail first. The weakened portion may be positioned so that it will be contacted by piercing edge 44 of piercing member 43. Such a weakened portion can be made by scoring, punching, etching and so forth. Now, after sample collector 40 has been fitted into test strip container 50 and buffer container 30 is turned to move the buffer container toward sample collector 40, piercing edge 44 strikes and ruptures that weakened portion. The buffer fluid can then flow out and mix with the sample. In another embodiment of the present invention, buffer container 30 can be rotated after piercing edge 44 strikes and ruptures the weaker portion, thereby further tearing the weakened portion and providing a larger opening for egress of the buffer fluid.

In an alternate embodiment of the present invention, buffer container 30 can be air-filled rather than liquid-filled. That is, buffer container 30 comprises an air-filled diluent bottle, which, upon compression expulses air from buffer container 30. The expulsed air then blows the sample into funnel collector (not shown).

Sample collector 40 can be provided with a lug which engages a matching notch (not shown) in test strip container 50. This will keep sample collector 40 from rotating within test strip container 50 when buffer container 30 joined thereto is twisted.

If desired, liquid flow out of buffer container 30 can be hastened by squeezing side walls 37 and 37' of compressible grip 36. This will deform and reduce the volume of buffer grip 36, expelling the buffer fluid therefrom.

If buffer container 30 has sealing rings in place of threads, then buffer container 30 can be urged downward by pressure on compressible grip 36. Again, pierceable membrane 38 will be pierced, and the buffer fluid expelled to come into contact with the sample.

In an alternate embodiment, sample collector 40 can be formed without a piercing member 43. Instead, pierceable membrane 38 of buffer container 30 can have a weakened portion (not shown) where it will, when stressed, fail first. The weakened portion can be made by scoring, punching, etching and so forth. Now, after sample collector 40 has been fitted into buffer container 30, compressible grip 36 of buffer container 30 is squeezed. This raises the pressure inside buffer container 30 until pierceable membrane 38 fails at the weakened portion. The buffer fluid can then flow out and mix with the sample, as already described.

The mixture of the buffer fluid and sample are drawn into funnel collector 20. Once the mixture of the buffer fluid and sample are in funnel collector 20, the mixture immediately and directly contacts test strip 60, which absorbs the mixture and displays an indicator. Once the mixed buffer fluid and sample have reacted with test strip 60, which can take place in known fashion, the appearance of test strip 60 may change, providing a visual indication of the result of the test being performed. This result can be seen through either a transparent window 55 in test strip container 50, or test strip container 50 itself if test strip container 50 is transparent.

With reference now to FIG. 5, the overall flow of buffer fluid and sample is in the direction of arrow A.

The sample testing device with funnel collector of the present invention may be employed to test subjects for a variety of medical conditions through use of the appropriate samples, buffer fluids and test strips. The manner of selecting a particular sample, buffer fluid and test strip to check for a condition of interest is itself known. Such medical conditions include, but are not limited to, hepatitis B, hepatitis C, HIV, tuberculosis, small pox, diphtheria and malaria. In addition, the instant testing system may be used to ascertain the presence of cardiovascular indicators in the blood of a subject thereby instantly alerting health care providers that the subject has recently suffered a cardiac event. Furthermore, the testing system may be used to determine the presence or absence of a drug in a subject's system. Examples of such drugs include, but are not limited to, alcohol, nicotine, and cocaine. The testing system may also be used by a law enforcement officer to readily ascertain if the blood alcohol content of a subject is above the legal limit. The testing system could also be used to identify the presence of various contaminants or pathogens. Examples of such pathogens or contaminants include, but are not limited to, anthrax, smallpox, botulism, Ebola virus, Legionnaire's disease, and so forth.

The testing system of the present invention has many advantages over existing testing systems. By way of non-limiting example, the present invention: 1) permits the delivery of a pre-defined volume of buffer and sample to the test strip; 2) is easy to use and 3) allows direct contact between the sample and the test strip.

Thus, while there have been shown and described and pointed out fundamental novel features of the invention as applied to exemplary embodiments thereof, it would be understood that various omissions and substitutions and changes in the form and details of the disclosed invention may be made by those skilled in the art without departing from the spirit of the invention. It is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope-of the invention that, as a matter of language, might be said to fall there between.

It also should be understood that the present invention is not intended to be limited to a method whose steps are performed in the order recited in the following claims. This invention encompasses the performance of those steps in other orders.

Thus, while there have been shown and described and pointed out fundamental novel features of the invention as applied to exemplary embodiments thereof, it would be understood that various omissions and substitutions and changes in the form and details of the disclosed invention may be made by those skilled in the art without departing from the spirit of the invention. It is the intention, therefore, to be limited only as indicated by the scope of the claims appended hereto.

What is claimed is:

1. A sample testing device comprising:
   a buffer container having an interior which receives a buffer fluid therein;
   a funnel collector having a securement;
   a test strip having an end held by said securement;
   a test strip container having a receptacle dimensioned and disposed to accommodate said funnel collector, so that when said funnel collector is accommodated by said test strip container, the test strip is disposed in said receptacle;
   a sample collector for holding a sample therein and which is shaped to receive said buffer container, said sample collector having a channeling member having a lumen, and a piercing member which, when said buffer container is placed in said sample collector, pierces said buffer container so that the buffer fluid in the interior of the buffer chamber contacts the sample and passes through the lumen to said funnel collector;
   wherein as the buffer fluid flows through the lumen of the sample collector the buffer fluid that has contacted the sample accumulates in said funnel collector and contacts said end of the test strip.

2. The sample testing device of claim 1, further comprising an anti-splashback disc adapted to be disposed within said funnel collector for controlling movement of said sample as the sample approaches said funnel collector and for preventing deflection of said sample off of said funnel collector.

3. The sample testing device of claim 1, wherein said funnel collector has at least one projection and at least one depression for engaging a corresponding structure of said test strip container.

4. The sample testing device of claim 1, wherein said buffer container has a threaded outer surface and said sample collector has a threaded inner surface, the threaded outer surface engaging the threaded inner surface when the buffer container and the sample collector are joined.

5. The sample testing device of claim 1, wherein said buffer container has a projection and said sample collector has a depression, the projection engaging the depression when the buffer container and the sample collector are joined.

6. The sample testing device of claim 1, wherein a top portion of said buffer container is bellowed, and wherein when said top portion is compressed, at least a portion of the buffer fluid is expelled from the buffer container.

7. The sample testing device of claim 1, wherein the buffer fluid is sealed within said buffer container.

8. The sample testing device of claim 1, wherein said buffer container comprises a compressible grip, and wherein when said grip is compressed, at least a portion of the buffer fluid is expelled from the buffer container.

9. The sample testing device of claim 1, wherein said test strip container has a viewing window through which the test strip is visible.

10. The sample testing device of claim 1, wherein said test strip container comprises a cover and a body, and said cover and said body are joined together.

11. The sample testing device of claim 10, wherein said cover and said body are joined together in fluid-tight fashion.

12. The anti-splashback disc of claim 2, wherein said sample testing device is comprised of a porous, non-reactive material.

13. A sample testing device comprising:
   a buffer container having an interior which receives a buffer fluid therein;
   a sample collector for holding a sample therein and having a top opening shaped to receive said buffer container, a bottom opening shaped to receive a funnel collector, and a piercing member positioned therein which, when said buffer container is placed in said top opening of said sample collector, pierces said buffer container so that the buffer fluid in the interior of the buffer container contacts the sample
   the funnel collector having both a top and a bottom portion, wherein said top portion of said funnel collector is shaped to fit into said bottom opening of said sample collector, and wherein said bottom portion of said funnel collector engages a test strip;
   a test strip container having a receptacle dimensioned and disposed to accommodate said funnel collector, so that when said funnel collector is accommodated by said test strip container, said test strip is disposed in said receptacle;
   wherein as said buffer fluid flows through said sample collector into the funnel collector, the buffer fluid that has contacted the sample passes to the funnel collector and contacts said test strip.

14. The sample testing device of claim 13, wherein said buffer container has a projection and said sample collector has a depression, the projection engaging the depression when the buffer container and the sample collector are joined.

15. The sample testing device of claim 13, wherein a top portion of said buffer container is bellowed, and wherein when said top portion is compressed, at least a portion of the buffer fluid is expelled from the buffer container.

16. The sample testing device of claim 13, wherein the buffer fluid is sealed within said buffer container.

17. The sample testing device of claim 13, wherein said test strip container has a viewing window through which the test strip is visible.

18. A sample testing device comprising:

a buffer container having an interior which receives a buffer fluid therein;

a funnel collector;

a test strip;

a test strip container having a receptacle dimensioned and disposed to accommodate said funnel collector, so that when said funnel collector is accommodated by said test strip container, the test strip engages said funnel collector and is disposed in said receptacle; and a sample collector for holding a sample therein and having a top opening shaped to receive said buffer container, a bottom opening, a pumping mechanism which draws air toward the pumping mechanism through an air passage, and a piercing member which, when said buffer container is placed in said sample collector, pierces said buffer container so that the buffer fluid in the interior of the buffer container contacts the sample and passes through the bottom opening to said funnel collector;

whereby when said pumping mechanism draws air through said air passage, a sample of a fluid is drawn into said sample collector through said bottom opening, wherein as the buffer fluid flows through the sample collector the buffer fluid contacts the sample and passes to said funnel collector and contacts said test strip.

19. The sample testing device of claim 18, wherein said buffer container has a projection and said sample collector has a depression, the projection engaging the depression when the buffer container and the sample collector are joined.

20. The sample testing device of claim 18, wherein a top portion of said buffer container is bellowed, and wherein when said top portion is compressed, at least a portion of the buffer fluid is expelled from the buffer container.

21. The sample testing device of claim 18, wherein the buffer fluid is sealed within said buffer container.

22. The sample testing device of claim 18, wherein said test strip container has a viewing window through which the test strip is visible.

23. The sample testing device of claim 18, wherein said air passage is located such that when said buffer container is fully inserted into said sample collector said air passage is blocked by said buffer container.

* * * * *